(12) United States Patent
Knecht

(10) Patent No.: US 10,231,887 B2
(45) Date of Patent: Mar. 19, 2019

(54) ABSORBENT INCONTINENCE ARTICLE HAVING A DIAPER COVER AND ABSORPTION INSERT

(71) Applicant: Paul Hartmann AG, Heidenheim (DE)

(72) Inventor: Theresia Knecht, Aalen (DE)

(73) Assignee: Paul Hartman AG, Heidenheim (DE)

( * ) Notice: Subject to any disclaimer, the term of this patent is extended or adjusted under 35 U.S.C. 154(b) by 500 days.

(21) Appl. No.: 14/654,173

(22) PCT Filed: Dec. 16, 2013

(86) PCT No.: PCT/EP2013/076710
§ 371 (c)(1),
(2) Date: Jun. 19, 2015

(87) PCT Pub. No.: WO2014/095727
PCT Pub. Date: Jun. 26, 2014

(65) Prior Publication Data
US 2015/0342793 A1    Dec. 3, 2015

(30) Foreign Application Priority Data

Dec. 21, 2012 (DE) .................. 10 2012 025 437

(51) Int. Cl.
*A61F 13/539* (2006.01)
*A61F 13/56* (2006.01)
(Continued)

(52) U.S. Cl.
CPC ........ *A61F 13/4906* (2013.01); *A61F 13/505* (2013.01); *A61F 13/539* (2013.01);
(Continued)

(58) Field of Classification Search
CPC ............ A61F 13/4906; A61F 13/49058; A61F 13/49061; A61F 2013/49063; A61F 2013/49065; A61F 2013/49066
(Continued)

(56) References Cited

U.S. PATENT DOCUMENTS 5,593,400 A    1/1997   O'Leary
5,853,405 A *  12/1998  Suprise ............. A61F 13/49017
                                                        604/391
(Continued)

FOREIGN PATENT DOCUMENTS

DE    10 2008 046 607 A1    5/2010
DE    10 2009 016 381 A1    10/2010
(Continued)

*Primary Examiner* — Susan S Su
(74) *Attorney, Agent, or Firm* — Dilworth & Barrese, LLP

(57) ABSTRACT

The application relates to an absorbent disposable incontinence diaper (2, 2a) of the open type having an at least three-part diaper cover (3) with an inner side (30) and an outer side (31), the diaper cover comprising a main part (4) and at least two separate rear side parts (16). The main part (4) has a front region (6), a rear region (8) and a crotch region (12), which lies therebetween in the longitudinal direction (21) and comes to lie between the legs of a user. The rear side parts (16) are arranged on both sides of the rear region (8) of the main part (4) in such a manner that said rear side parts (16) are fixed in first overlap regions (40) with the outer side thereof on the inner side of the main part (4) along rear, lateral longitudinal edges (20). The rear side parts (16) extend in the transverse direction (22) over the rear lateral longitudinal edges (20) of the main part (4) and have closure means (10). The main part (4) and the rear side parts (16) comprise a nonwoven material or are made therefrom. The diaper cover (3) extends continuously over a length L1 from a front end (33) of the diaper cover (3) via the crotch region (12) to a rear end (34) of the diaper cover (3). An absorption insert (5) having an inner side and an outer side is arranged on the inner side (30) of the diaper cover (3), the absorption insert (5) comprising a liquid-impermeable back sheet (62) and a top sheet (64), between which an absorption body (7) is arranged. The absorption insert (5) extends into the first
(Continued)

overlap regions (40) and is fixed there at least in some sections with the outer side thereof on the diaper cover (3). The absorption insert (5) has a length L2, where L2<L1.

21 Claims, 4 Drawing Sheets

(51) Int. Cl.
    *A61F 13/49*     (2006.01)
    *A61F 13/505*     (2006.01)

(52) U.S. Cl.
    CPC .............. *A61F 13/5638* (2013.01); *A61F 2013/49074* (2013.01); *A61F 2013/49077* (2013.01); *A61F 2013/5055* (2013.01); *F04C 2270/041* (2013.01)

(58) Field of Classification Search
    USPC .................................. 604/358–392
    See application file for complete search history.

(56) References Cited

U.S. PATENT DOCUMENTS

| | | | | |
|---|---|---|---|---|
| 6,579,275 | B1* | 6/2003 | Pozniak | A61F 13/496 604/385.01 |
| 6,972,012 | B1* | 12/2005 | Pozniak | A61F 13/496 604/386 |
| 8,152,788 | B2* | 4/2012 | Beckert | A61F 13/51401 604/367 |
| 8,715,263 | B2 | 5/2014 | Wenzel et al. | |
| 2005/0148980 | A1* | 7/2005 | Fitton | A61F 13/505 604/385.3 |
| 2009/0299322 | A1* | 12/2009 | Faulks | A61F 13/551 604/386 |
| 2010/0030176 | A1* | 2/2010 | Beckert | A61F 13/51401 604/367 |
| 2010/0268183 | A1* | 10/2010 | Een | A61F 13/15739 604/385.01 |
| 2010/0318055 | A1* | 12/2010 | Hornung | A61F 13/49014 604/385.31 |
| 2011/0146892 | A1* | 6/2011 | Ostertag | A61F 13/15699 156/204 |
| 2011/0288518 | A1* | 11/2011 | Roe | A61F 13/49004 604/385.14 |
| 2011/0313382 | A1* | 12/2011 | Ashton | A61F 13/49014 604/365 |
| 2012/0028777 | A1* | 2/2012 | Knecht | A61F 13/15699 493/393 |
| 2012/0157955 | A1 | 6/2012 | Ashton et al. | |
| 2012/0184937 | A1* | 7/2012 | Sablone | A61F 13/62 604/385.24 |
| 2012/0271267 | A1* | 10/2012 | Love | A61F 13/49012 604/385.101 |
| 2014/0018764 | A1* | 1/2014 | Johnston | A61F 13/49006 604/385.16 |
| 2014/0324010 | A1* | 10/2014 | Oku | A61F 13/494 604/385.16 |
| 2015/0157251 | A1* | 6/2015 | Nelson | A61F 13/15699 600/362 |
| 2015/0182388 | A1* | 7/2015 | Katsuragawa | A61F 13/49014 604/385.29 |
| 2015/0245959 | A1* | 9/2015 | Nelson | A61F 13/5644 604/391 |

FOREIGN PATENT DOCUMENTS

| | | |
|---|---|---|
| JP | 2001 087312 A | 4/2001 |
| WO | 99/33427 A1 | 7/1999 |
| WO | 2007/000315 A1 | 1/2007 |
| WO | 2010/108660 A1 | 9/2010 |
| WO | 2011/040046 A1 | 4/2011 |
| WO | 2012/054591 A1 | 4/2012 |

* cited by examiner

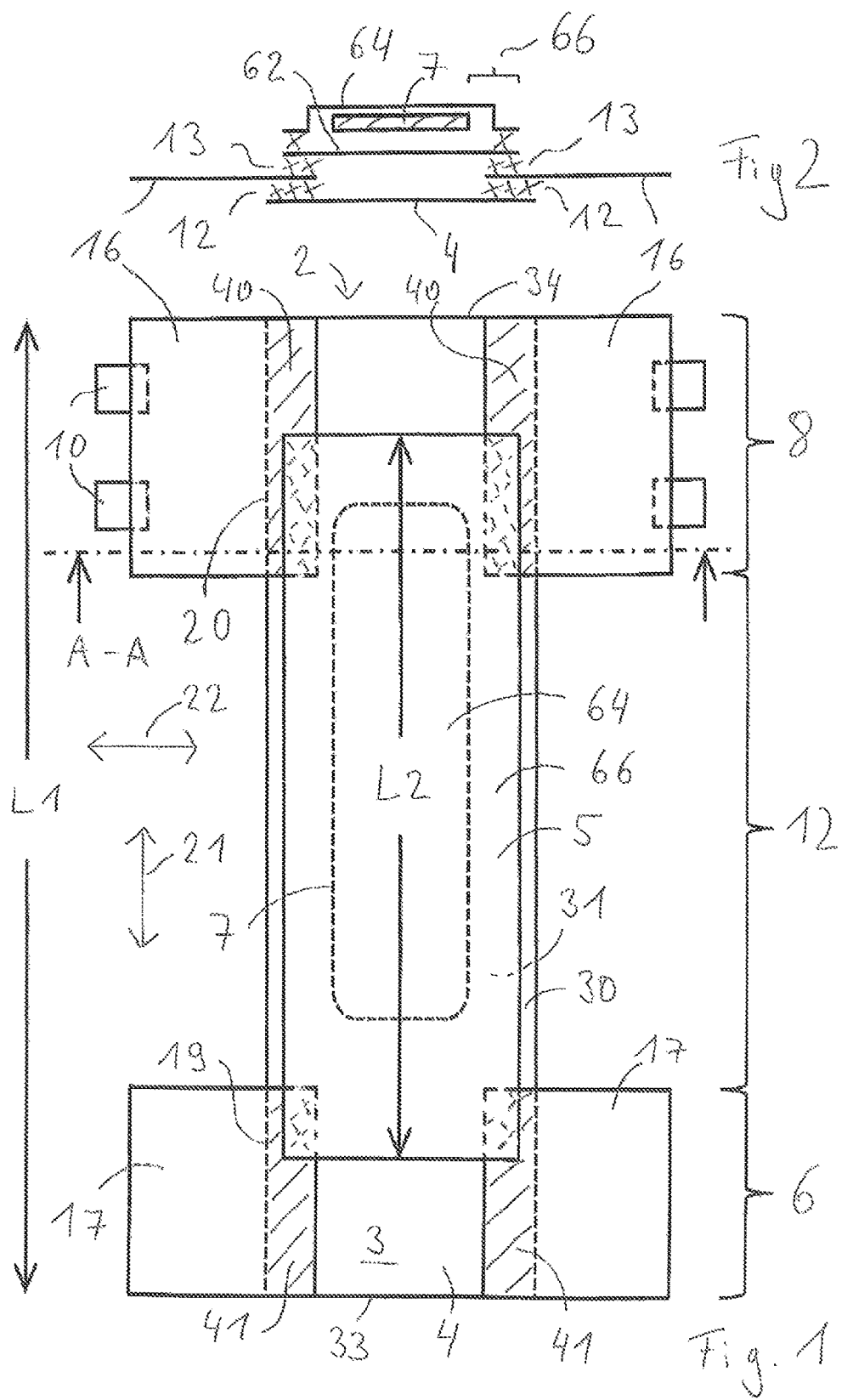

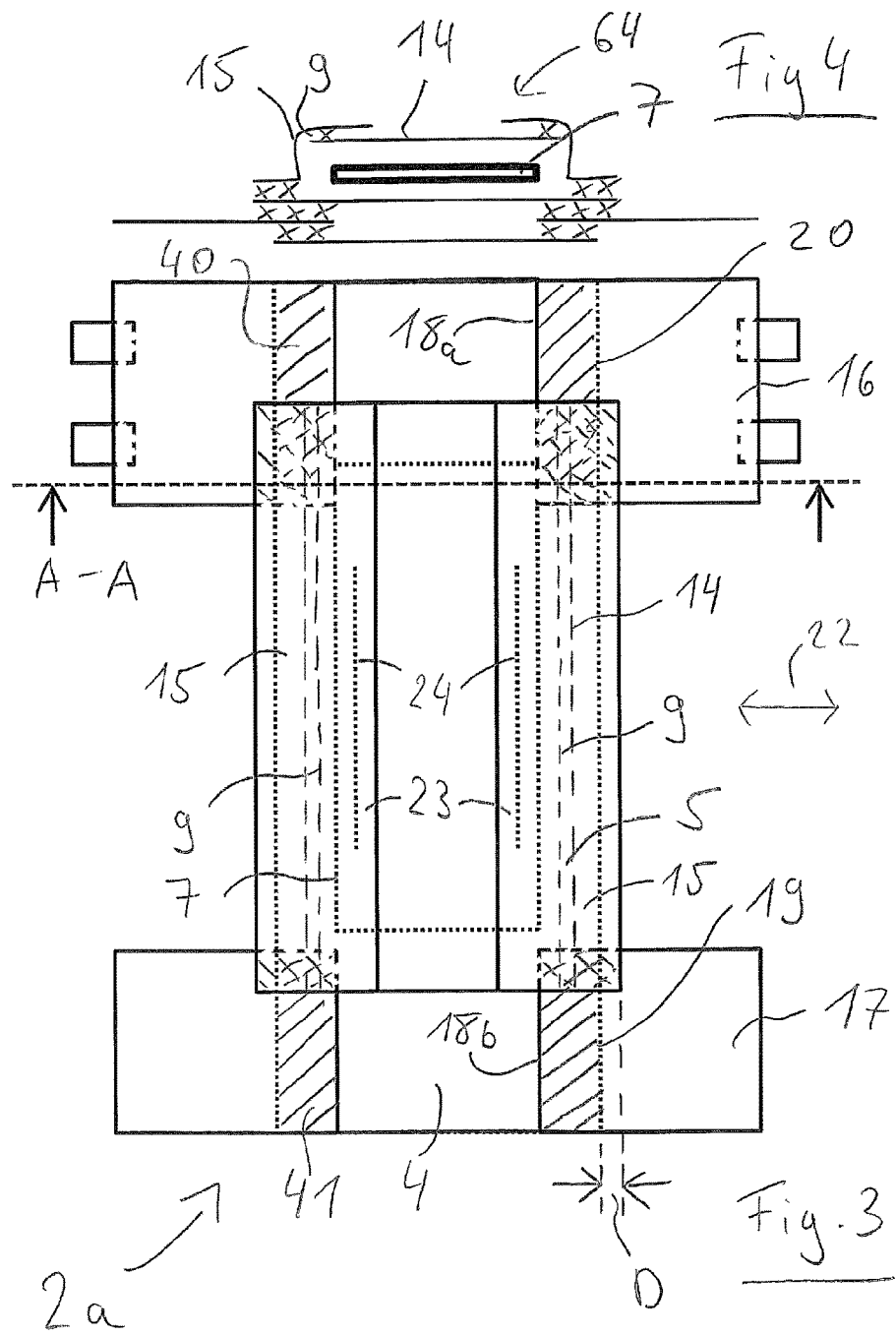

ABSORBENT INCONTINENCE ARTICLE HAVING A DIAPER COVER AND ABSORPTION INSERT

BACKGROUND OF THE INVENTION

The present invention relates to an absorbent disposable incontinence diaper of the open type, having a rear region, a front region, and a crotch region lying therebetween, and having a main part with an inner side which when in use faces the body and an outer side which when in use faces away from the body, and having discrete lateral parts which are joined onto the first and second lateral periphery of the main part. The disposable incontinence diaper is envisaged for adults and is configured as a disposal diaper, that is to say conceived for single use.

Disposable incontinence diapers of this type are also known from WO2004/105668A1, for example.

In disposable incontinence diapers of this type the mentioned lateral parts may be formed from another material than the main part. For example, the lateral parts, which often are also referred to as "ears" of the disposable incontinence diaper may be configured so as to be breathable, in particular so as to be permeable to air and water vapor, whereas the main part is implemented so as to be impermeable to fluid.

In order for the disposable incontinence diaper to be closed, the lateral parts, which preferably are joined in an unreleasable manner to the rear region, are folded onto the stomach side of the user and there, either by way of the outer side of the front region of the main part or by way of the outer side of the lateral parts of the front region, connected in a releasable manner.

In as far as a disposable incontinence diaper of this type is equipped with mechanical closure aids, the problem arises that a corresponding landing region which has to be engageable with the Velcro-type hooks has to be provided on the outer side of the front region of the diaper for the closure aids which are usually disposed on the rear lateral parts and mostly implemented as Velcro-type hooks.

However, the outer side of the main part of such disposable incontinence diapers is usually formed using a film material, in order to prevent leakage of fluid through the absorbent element to the outside. The lateral parts of disposable incontinence diapers of this type preferably are formed from smooth non-woven materials, in order to improve the skin friendliness of the diaper where no reliable fluid barrier is required. A landing area for securing the Velcro-type hooks on the outer side of the front region of the diaper would thus require the application of an additional material, in particular a textile loop component which is known per se. However, loop components of this type would have to extend across vast parts of the front region of the outer side of the diaper, in order to ensure the high degree of flexibility in size adjustment required in disposable incontinence diapers (diapers for adults). Since textile loop components represent a substantial cost factor, a solution of this type is already precluded for economic reasons.

Furthermore, it has been demonstrated in disposable incontinence diapers of the known type that the subjective perception of diaper comfort differs significantly, despite the skin friendly lateral parts which are permeable to air and water vapor.

It has already been proposed in DE102009016381A1 to form the main part as an integral unit from a top sheet, a non-woven film laminate as a back sheet, and an absorbent body disposed therebetween. Four discrete lateral parts are joined onto this main part at the rear and the front.

SUMMARY OF THE INVENTION

It is an object of the present invention to provide an alternative disposable incontinence diaper which can be economically manufactured and moreover offers the user of the disposable incontinence diaper a greater degree of wear comfort.

Proposed is, therefore, an absorbent disposable incontinence diaper of the open type, having an at least tripartite diaper shell which has an inner side and an outer side, wherein the diaper shell comprises a main part and at least two separate rear lateral parts, wherein the main part has a front region, a rear region, and a crotch region which in the longitudinal direction is therebetween and comes to lie between the legs of a user, and wherein the rear lateral parts are disposed on both sides of the rear region of the main part in such a manner that the rear lateral parts, by way of their outer side, are fixed in first overlapping regions on the inner side of the main part along rear lateral longitudinal peripheries, and wherein the rear lateral parts in the transverse direction extend beyond the rear lateral longitudinal peripheries of the main part, and wherein the rear lateral parts have closure means, and wherein the main part and the rear lateral parts comprise a non-woven material or are formed therefrom, and wherein the diaper shell continuously extends across a length L1, from a front end of the diaper shell across the crotch region to a rear end of the diaper shell, and wherein an absorbent insert having an inner side and an outer side is disposed on the inner side of the diaper shell, wherein the absorbent insert comprises a fluid-impermeable back sheet and a top sheet between which an absorbent body is disposed, wherein the absorbent insert extends into the first overlapping regions and there, by way of its outer side, is at least in portions fixed on the diaper shell, wherein the absorbent insert has a length L2, and wherein L2<L1 applies. The longitudinal extent of the absorbent insert thus is smaller than that of the diaper shell.

Thus, the diaper shell, being an at least tripartite (2 lateral parts and the main part) non-woven composite, forms a diaper frame which is extremely comfortable to wear.

The inside longitudinal peripheries of the lateral parts overlie the rear longitudinal peripheries of the main part in the first overlapping regions and there, by way of their outer side, are fixed on the inner side of the main part, preferably in an unreleasable manner.

The inner side of a flat material described above or below is in each case to be understood to be that side of the flat material which, when the diaper is in use, faces the body. Accordingly, the outer side of a flat material described above or below is in each case to be understood to be that side which, when the diaper is in use, faces away from the body.

The flat material which forms the main part of the diaper shell is substantially entirely composed of a non-woven material. Therefore, the main part across its entire extent may be designed so as to be permeable to air. By contrast, the absorbent insert which is integrally configured comprises a film material as a back sheet. On account thereof, it is ensured that no fluid can pass from the absorbent body to the outside during use. Since the longitudinal extent of the absorbent insert L2 is smaller than the longitudinal extent L1 of the diaper shell, the diaper according to the invention may be produced with significantly less investment in materials, as compared with the disposable incontinence diaper disclosed in DE102009016381A1. Moreover, the permeability to air of the diaper shell during use is fully maintained outside the planar extent of the absorbent insert. Moreover, the inventors have recognized that the composite of the diaper shell may be further reinforced when the first overlapping regions of the diaper shell, that is to say the regions in which the main part and the rear lateral parts are connected in an unreleasable manner in an overlapping configuration, are at least partly overlaid by the absorbent insert, that is to say when the absorbent insert extends into the first overlapping regions and, by way of its outer side, is fixed there on the inner side of the diaper shell, that is to say fixed on an inner side of the lateral parts in the overlapping region. On account thereof, the risk of the lateral parts being inadvertently torn out of the non-woven composite which is composed of the lateral parts and the main part is significantly reduced.

According to a refinement of the invention it is provided that lateral parts are also joined onto the left and right (both sides) of the front region of the main part, in the same way as on the rear region, that is to say in such a manner that the front lateral parts in second overlapping regions are connected to the lateral peripheral regions of the main part. In such a case, the absorbent insert preferably also extends into the second overlapping regions and, by way of its outer side, is fixed there on an inner side of the diaper shell.

Preferably, the back sheet and/or the top sheet in the transverse direction and/or in the longitudinal direction form an overhang over the absorbent body. In such a case, it is in particular part-regions of the overhang of the absorbent insert which extend into the first and/or second overlapping regions.

In respect of reinforcing the non-woven composite which forms the main part it has proven advantageous for in each case at least 20%, particularly at least 30%, furthermore particularly at most 90%, furthermore particularly at most 80% of the area of the first overlapping regions to be connected to the absorbent insert.

In order to determine dimensions of components of the disposable incontinence diaper and the area proportions, the disposal incontinence diaper is measured in a state in which it is spread out in a planar manner.

The ratio of the lengths L2/L1 is preferably smaller than 0.9, particularly smaller than 0.8, furthermore particularly smaller than 0.7, furthermore particularly larger than 0.3.

Preferably the proportion of that area of the second overlapping regions that is connected to the absorbent insert is smaller than the proportion of that area of the first overlapping regions that is connected to the absorbent insert. Due to the closure means being disposed on the rear lateral parts and the associated risk of the bond between the lateral parts and the main part being destroyed by tensile forces which are introduced by way of the closure means into the overlapping regions, it has proven advantageous for the first overlapping regions to be more heavily reinforced than the second overlapping regions.

It is advantageous for in each case at least 10%, particularly at least 20%, furthermore particularly at most 85%, furthermore particularly at most 75% of the area of the second overlapping regions to be connected to the absorbent insert.

In order for the non-woven composite forming the main part to be reinforced, it has proven particularly advantageous for the absorbent insert to completely overlie the first and/or the second overlapping regions in the transverse direction. To this end, the absorbent insert in the transverse direction, at least in the back region of the diaper shell, but in particular continuously across its entire longitudinal extent, is preferably configured so as to be wider than the main part of the diaper shell. Preferably the absorbent insert in the transverse direction outwardly extends by the dimension D beyond the rear, in particular beyond the rear and front, lateral longitudinal peripheries of the main part, wherein D preferably is 0.5 to 10.0 cm, particularly 1.0 to 8.0 cm, furthermore particularly 1.2 to 5.0 cm.

Preferably, the absorbent insert thus overlaps both a respective inner longitudinal periphery of the rear lateral parts as well as a respective rear lateral longitudinal periphery of the main part along at least an imaginary line running in the transverse direction, and at least along this line is connected to the inner side of the diaper shell, that is to say fixed thereonto.

The outer side of the absorbent insert may preferably also be connected to the inner side of the diaper shell in a fully planar manner, preferably in further regions, i.e. also outside the first or second overlapping regions, particularly by way of a continuous or discontinuous application of a hot-melt adhesive, for example in the form of a helical adhesive-spray pattern.

Furthermore preferably, the planar extent of the absorbent body and the arrangement thereof are implemented in such a manner that the absorbent body does not extend into the first and/or second overlapping regions.

Advantageously, the absorbent insert can have a leg-opening contour which is, at least in portions, rounded, that is to say curved, in such a manner that the absorbent insert in a region which is level with the transverse center axis of the diaper shell has a smaller transverse extent than in the rear region and/or the stomach region.

The rear lateral parts and/or the front lateral parts and/or the main part of the diaper shell in each case may be formed from rectangular portions.

Furthermore advantageously, however, the diaper shell can have a leg-opening contour which is, at least in portions, rounded, that is to say curved, in such a manner that the diaper shell in a region which is level with the transverse center axis of the diaper shell has a smaller transverse extent than in the rear region and/or the stomach region. Here, the main part and/or the front lateral parts and/or the rear lateral parts may have a curved leg-opening contour.

In the first and/or second overlapping regions the lateral parts by way of their outer side are connected in an overlapping configuration to the inner side of the diaper shell, that is to say joined to one another. Advantageously, joining to one another may be performed by way of joining means which are known per se, such as adhesives, particularly hot-melt adhesives, by embossing, thermal calendaring, or by welding, particularly by ultrasonic welding.

Joining of the outer side of the absorbent insert to the inner side of the diaper shell in the first and/or second overlapping regions likewise is advantageously performed by way of adhesives, particularly hot-melt adhesives, by embossing, thermal calendaring, or by welding, particularly by ultrasonic welding.

Closure means are provided on the rear lateral parts. The closure means have, for example, adhesive closure elements, but particularly mechanical closure elements, such as Velcro-type hooks. Particularly preferably, the closure means have both, adhesive as well as mechanical closure elements. To this end, adhesively bonding regions and mechanically bonding regions which are arranged next to one another on one respective closure strip are advantageously provided, such as is described in EP321232A1, for example.

In order for the disposable incontinence diaper to be fixed as per its intended use on the body of a person, the closure means are fixable to the outer side of a front region of the diaper, wherein the user has the possibility to adapt the diaper to the anatomical profile of the user, particularly to the hip circumference of the user of the diaper. As opposed to the known fix-point fasteners, it is provided to this end that the user has the possibility of varying the positioning of the closure means in respect of the transverse direction on the outer side of a front region of the diaper. Preferably, the closure means are fixable on the entire outer side of the front region of the main part. Furthermore preferably, the closure means are fixable on the entire outer side of the front lateral parts, in as far as the disposable incontinence diaper has front lateral parts.

According to a preferred embodiment it is provided that the closure means of the rear lateral parts for fixing the disposable incontinence diaper as per its intended use on the body of a person are fixable in a releasable manner at least in portions on both the outer side of the main part in the front region, as well as the outer side of the front lateral parts. Preferably, the cohesive forces between the closure means and the outer side of the front lateral parts are greater here than the cohesive forces between the closure means and the outer side of the main part. In most cases, this prompts the user to fix the closure means on the front lateral parts, benefiting the fit of the diaper. The cohesive forces, determined as cross-stomach cohesive forces, between the closure means, which have in particular mechanical closure aids, and the outer side of the main part, are preferably 20 to 57 N/25 mm, particularly 25 to 50 N/25 mm, measured according to the test method described in EP1915977A1.

It has furthermore proven advantageous for the front and/or rear lateral parts and/or the main part to be formed from a non-woven material which contains at least one component of the recipe based on a thermoplastic polymer. The non-woven materials may contain fibres of PE, PP, PET, rayon, cellulose, PA, and mixtures thereof. Bi-component or multi-component fibres are also conceivable and advantageous. Carded non-wovens, spun non-wovens, water-jet needled non-wovens, SM non-wovens, SMS non-wovens, SMMS non-wovens, or else laminates made from one or more of these types of non-wovens are advantageous in particular, wherein S indicates spun-bond and M indicates melt-blown non-woven layers. Spun non-wovens are particularly preferable, since they have high strength in the longitudinal and transverse direction and thus are capable of resisting particularly well the shear forces which act upon them as a result of the engagement of mechanical closure aids which may optionally be present.

Advantageously, the rear later parts differ from the front lateral parts and/or the main part in respect of at least one, particularly at least two, furthermore particularly at least three, and furthermore particularly at least four of their primary properties, selected from the group of type of material, area weight, breathability, density, elongation capability, closure force, planar extent, thickness, color.

Type of material: It has proven advantageous for the front lateral parts to be formed from a softer, more skin friendly non-woven material than the rear lateral parts, since the front lateral parts as per the intended use come to lie on the inside against the body when the diaper is put on. It may furthermore be advantageous for the rear lateral parts to be formed from a material with higher tensile strength, since the closure means are attached to the rear lateral parts and strong tensile forces act via the closure means on the lateral parts when the diaper is put on. Preferable differentiations in respect of the type of material may be implemented by way of the type of fiber used, the method of non-woven formation, or laminate formations.

Area weight: The abovementioned requirements preferably at least in proportions may be achieved by way of differentiating the area weight measured in $g/m^2$. Preferably, the area weight of the front lateral parts differs by at least 10%, particularly at least 20%, and furthermore particularly by at least 30% from that of the rear lateral parts. Furthermore preferably, the area weight of the front and/or rear side parts differs by at least 10%, particularly by at least 20%, and furthermore particularly by at least 30% from the area weight of the main part of the diaper shell.

The area weight of the front and/or rear lateral parts and/or of the main part of the diaper shell preferably is 10 to 60 $g/m^2$, particularly 12 to 45 $g/m^2$, furthermore particularly 15 to 40 $g/m^2$, and furthermore particularly 18 to 35 $g/m^2$.

Breathability: Since the subjective perception of the compromise in wear comfort differs from target group to target group (for example, from bedridden patients to mobile patients), it may be advantageous for breathability to be configured to be higher either in the front or the rear lateral parts. Preferably, breathability measured as permeability to water vapor (WVTR according to DIN 53 122-1, Edition: 2001-08) of the front lateral parts differs from that of the rear lateral parts by at least 5%, particularly by at least 10%, and furthermore particularly by at least 20%.

Preferably, the breathability of the front and/or rear lateral parts here is at least 1000 $g/m^2/24$ h, particularly at least 1500 $g/m^2/24$ h, furthermore preferably at least 2000 $g/m^2/24$ h.

Density and thickness: The subjectively perceived softness of the lateral-part material and thus a substantial component of wear comfort advantageously may also be controlled by way of differentiating the density and/or the thickness of the material. Preferably, the thickness measured in mm, determined at a test pressure of 0.5 kPa, and/or the density measured in $g/cm^3$, determined from the variables of area weight and thickness of the material, of the front lateral parts differs from the density and/or thickness of the rear lateral parts by at least 15%, particularly by at least 20%, and furthermore particularly by at least 25%. Furthermore preferably the thickness and/or the density of the front and/or rear lateral parts differs from the density and/or the thickness of the main part of the diaper shell by at least 15%, particularly by at least 20%, and furthermore particularly by at least 25%.

Elongation capability: Elongation is understood in the present case to be the ratio of an increase in length of a lateral part of the disposable incontinence diaper as a result of a force acting thereon to the original length. During the use of disposal incontinence diapers of this type forces act on the lateral parts in particular in the circumferential direction, that is to say the transverse direction of the diaper. Thus, elongation capability as a property is understood as the extent of the elongation of the lateral part when a force acts in the transverse direction of the diaper. This means, the higher the extent of elongation, the higher elongation capability. Preferably, a rear lateral part when subjected to force which is usual when the diaper is in use has greater elongation capability than a front lateral part. In particular, according to the test method described in DE102005048868A1, a rear lateral part subjected to a force of 45 N has higher elongation than a front lateral part. Preferably in the case of being subjected to a force of 45 N, a rear lateral part has elongation of at least 20%, particularly at least 25%, and furthermore particularly at least 30%. By contrast, a front lateral part being subjected to a force of 45 N has elongation of only preferably at most 15%, particularly at most 10%, and furthermore particularly at most 8%. Preferably, at least one rear lateral part is elastically elongatable at least in the transverse direction. Elongation capability of the lateral part is described as being elastic if, in the case of being briefly (2 to 5 seconds) subjected to a force, elongation of at least 40% is possible and, once this force has been released, an elongation (lasting elongation) of at most 20% remains. In an advantageous refinement of the invention the elastic elongation capability of a rear lateral part in the transverse direction is at least 40%, particularly at least 50%. According to a further concept of the invention, the absolute extent of the elastic elongation of a rear lateral part is at least 3 cm, particularly at least 5 cm, and furthermore particularly at least 7 cm.

Closure force: Closure force of the lateral parts is understood to be the cohesive force between the closure means of the rear lateral parts and the outer side of the lateral parts. Preferably, the cohesive forces between the closure means and the outer side of the rear lateral parts here are smaller than the cohesive forces between the closure means and the outer side of the front lateral parts. In an advantageous way, this leads to the user preferably fixing the closure means on the front lateral parts, which significantly benefits fit and wear comfort of the diaper. The cohesive forces mentioned above or below are preferably determined as cross-stomach cohesive forces. The cross-stomach cohesive forces in the context of this invention are to be determined according to the test method described in EP1915977A1. The cohesive forces which have been determined as cross-stomach cohesive forces between the closure means having in particular mechanical closure aids and the outer side of the front lateral parts are preferably 58 to 90 N/25 mm, particularly 60 to 80 N/25 mm.

The cross-stomach cohesive forces between the closure means having in particular mechanical closure aids and the outer side of the rear lateral parts are preferably smaller than the cross-stomach cohesive forces between the closure means and the outer side of the front lateral parts; however, they are preferably nevertheless at least 15 N/25 mm, particularly at least 30 N/25 mm.

Planar extent: In a refinement of the invention it proves advantageous for the rear lateral parts to have a larger planar extent, preferably a planar extent which is larger by at least 10%, particularly by at least 15%, than the front lateral parts. In particular, the length of the rear lateral parts, that is to say the extent of the latter in the longitudinal direction of the diaper, may be at least 10 cm, particularly at least 15 cm, furthermore particularly at least 18 cm, and furthermore particularly at least 22 cm.

Furthermore, it proves advantageous for the length of the rear lateral parts to be at least 10%, particularly at least 15%, furthermore particularly at least 20%, and furthermore particularly at least 22% of the total length L1 of the diaper shell. Advantageously, the total length L1 of the diaper shell is 50 to 120 cm, particularly 60 to 110 cm, and furthermore particularly 70 to 110 cm.

Furthermore, it proves advantageous for the front lateral parts to have a smaller longitudinal extent, particularly a longitudinal extent which is smaller by at least 5%, furthermore particularly by at least 10%, furthermore particularly by at least 15%, and furthermore particularly by at most 50% than the rear lateral parts.

Furthermore, it proves advantageous for the width of the lateral parts, that is to say the extent of the lateral parts in the transverse direction beyond the rear lateral longitudinal periphery of the main part, to be 10 to 40 cm, particularly 12 to 30 cm, furthermore particularly 13 to 25 cm. Preferably, the front lateral parts have the same width as the rear lateral parts.

Color: Finally, it may be advantageous for the front lateral parts to be different from the rear lateral parts in terms of color. This may also clarify for the user the functioning of the front lateral parts as a preferred landing area of the closure means.

The modular construction of the disposable incontinence diapers according to the invention allows the diaper manufacturer to meet various user requirements, particularly in respect of fit and absorptivity, without having to excessively individualize production technology for manufacturing the disposable incontinence diapers.

Therefore, it is provided according to a further concept of the invention to provide a group of disposable incontinence diapers which comprises at least first and second disposable incontinence diapers according to the invention as described above, wherein the first and second disposable incontinence diapers in respect of the dimensions in the longitudinal and/or transverse directions, in particular also in respect of further properties such as material composition or area weight of the main part and/or the rear lateral parts, in particular in respect of all properties have an identical diaper shell, wherein the absorbent insert of the first disposable incontinence diapers differs from the absorbent insert of the second disposable incontinence diapers at least in one property selected from the group of dimensions in the longitudinal and/or transverse directions, absorptivity (measured according to ISO 11948-1 (1996)), material composition, layer construction, elastification.

According to a further concept of the invention it is provided to provide a group of disposable incontinence diapers which comprises first and second disposable incontinence diapers according to the invention, wherein the first and second disposable incontinence diapers have an absorbent insert which is identical in respect of the dimensions in the longitudinal and/or transverse directions, and preferably also in respect of further properties such as material composition or area weight, furthermore particularly in respect of all properties, wherein the diaper shell of the first disposable incontinence diapers differs from the diaper shell of the second disposable incontinence diapers at least in one property selected from the group of dimensions in the longitudinal and/or transverse directions, material composition, area weight of the main part and/or of the rear lateral parts.

BRIEF DESCRIPTION OF THE DRAWINGS

In the figures:

FIG. 1 shows a plan view of a disposable incontinence diaper according to the invention;

FIG. 2 shows a sectional view along A-A of the disposable incontinence diaper according to FIG. 1;

FIG. 3 shows a plan view of a further disposable incontinence diaper according to the invention;

FIG. 4 shows a sectional view along A-A of the disposable incontinence diaper according to FIG. 3;

DESCRIPTION OF THE PREFERRED EMBODIMENTS

Figure 5:
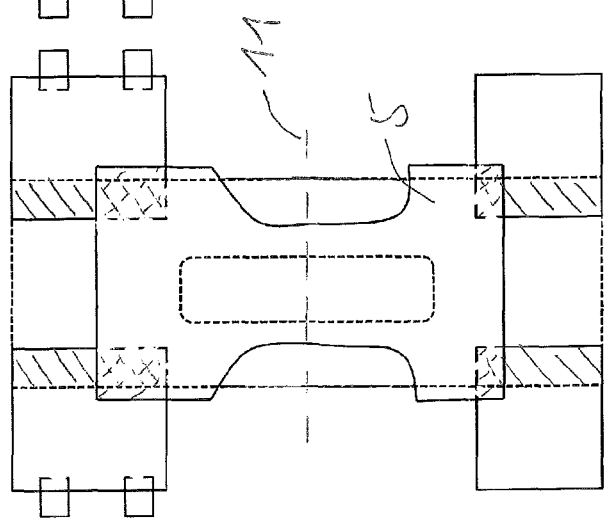
FIGS. 5 to 7 show plan views of further disposable incontinence diapers according to the invention having a contoured leg opening.

FIG. 1 and FIG. 2 (cross section along A-A) in a schematic manner which is not true to scale show a plan view of the inner side, that is to say that side that faces the body, of an absorbent disposable incontinence diaper 2 in a just unfolded state. The disposable incontinence diaper 2 comprises an outer diaper shell 3 having a inner side 30, which when in use faces the body, and an outer side 31, which when in use faces away from the body. The diaper shell 3 having the length L1 comprises a rectangular main part 4 with a front region 6, a rear region 8, and a crotch region 12 which in the longitudinal direction 21 lies therebetween. Moreover, the diaper shell 3 comprises two rear rectangular lateral parts 16 and two front rectangular lateral parts 17, and is thus configured in five parts. The lateral parts 16, 17, and the main part 4 are formed from non-woven materials. The rear lateral parts 16 in the rear region 8, by way of their outer side, are fixed in an overlapping configuration on the inner side 30 of the main part 4 in the first overlapping regions 40 (illustrated in a hatched manner), and in the transverse direction 22 extend beyond rear lateral longitudinal peripheries 20 of the main part 4. Accordingly, the front lateral parts 17 are fixed in the front region 6 on the main part 4 in second overlapping regions 41, and in the transverse direction 22 extend beyond front lateral longitudinal peripheries 19 of the main part 4. In the illustrated case, the connection between the lateral parts 16, 17 and the main part 4 in first and second overlapping regions is performed by way of a first application of hot-melt adhesive 12.

The diaper shell 3 continuously extends across a length L1, from a front end 33 of the diaper shell 3 via the crotch region 12 to a rear end 34 of the diaper shell 3. Moreover, the disposable incontinence diaper has an absorbent insert 5 having the length L2, which is fixed on the inner side of the diaper shell. The absorbent insert 5 has a fluid-impermeable back sheet 62 and a top sheet 64, an absorbent body 7 being disposed therebetween. The absorbent body 7 is suitable for receiving and permanently storing in particular aqueous bodily fluids, such as urine. Said absorbent body 7 may contain so-called SAP (super-absorbent polymer) and/or cellulose fibers in a manner which is usual per se. The absorbent body 7 moreover may be constructed in one layer or in multiple layers. The top sheet 64 is formed from a fluid-permeable non-woven material. The back sheet 62 is formed from a film material. The top sheet 64 and the back sheet 62 overlie the absorbent body 7 and in the longitudinal direction 21 and transverse direction 22 extend beyond the absorbent body 7, so as to form an overhang 66. The overhang 66 of the absorbent insert 5 extends into the first and second overlapping regions 40, 41 and there (within the first and second overlapping regions, respectively) at least in portions is connected to the rear and front lateral parts 16, 17. This is performed in such a manner that the outer side of the respective regions of the overhang 66 is fixed on the inner side of the diaper shell 3, specifically on the inner side of the respective overlapping regions. In the illustrated case, this connection is performed by means of a second application of hot-melt adhesive 13 (identified in FIG. 1 by an interrupted hatching). That area of the first overlapping regions 40 that is overlaid by the overhang 66 and connected there to the overhang 66 is in each case 20 cm². The area of the first overlapping regions is in each case 60 cm². The proportion of that area of the first overlapping regions that is overlaid and connected to the absorbent insert 5 is in each case (that is to say in each of the two overlapping regions 40) thus 33⅓%. As can be seen from FIG. 1, the proportion of that area of the second overlapping regions that is overlaid by the overhang 66 and connected there to the overhang 66 is significantly smaller: The area of the second overlapping regions 41 here is in each case 45 cm²; that area of the second overlapping regions 41 that is overlaid by the overhang and connected there is in each case 9 cm². The proportion of that area of the second overlapping regions that is overlaid and connected to the absorbent insert thus is in each case 20%.

The outer side of the absorbent insert may preferably also be connected in a fully planar manner to the inner side of the diaper shell 3, preferably in further regions, i.e. also outside the overlapping regions 40, 41, in particular by way of a continuous or discontinuous application of hot-melt adhesive, for example in the form of a helical spray-adhesive pattern.

Figure 8:
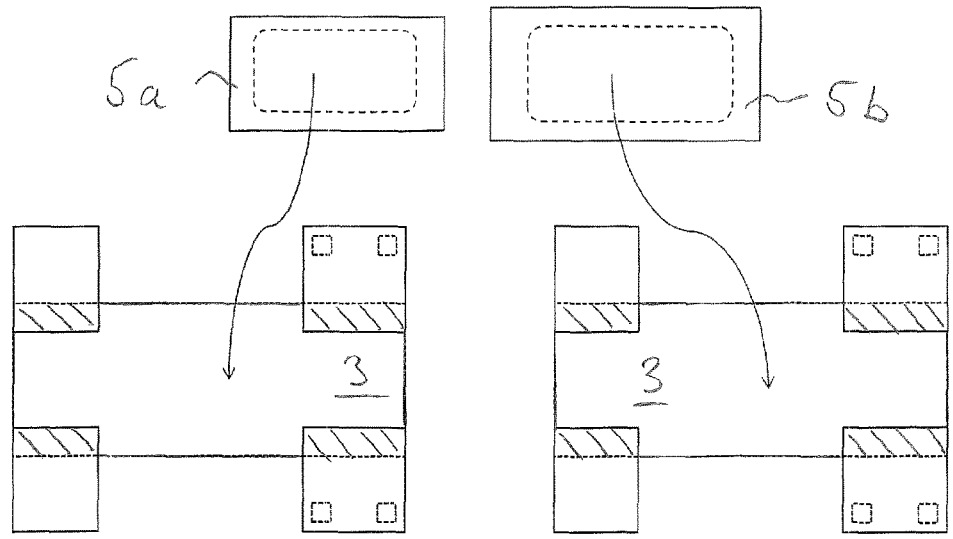
FIG. 8 shows schematic illustrations of the provision of a group of first and second disposable incontinence diapers according to the invention.
Figure 9:
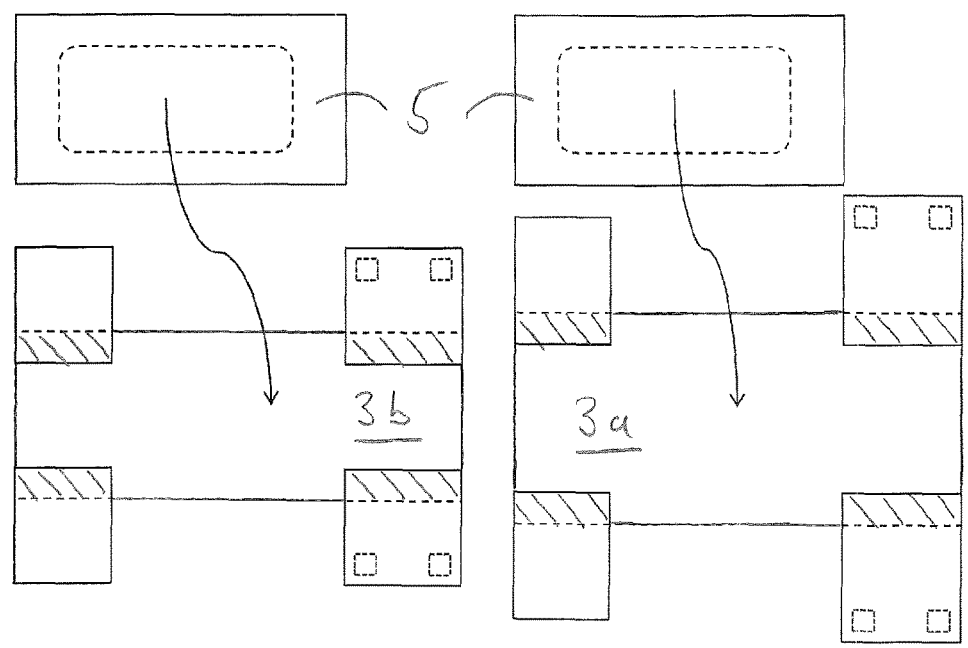
FIG. 9 shows schematic illustrations of the provision of a further group of first and second disposable incontinence diapers according to the invention.

The rear lateral parts 16 have closure means 10 with Velcro-type hooks, by means of which the rear lateral parts 16 when in use are fixable in a releasable manner on the outer side of the front lateral parts 17. Moreover, the closure means 10 are preferably fixable on the outer side of the main part 4 in the front region. This allows the user to also put on a diaper which is tailored so as to be really too large for this wearer, in that the hip circumference of the diaper is heavily reduced when the diaper is being put on. As is indicated in FIG. 1, the closure means 10 may be configured as closure tapes which extend beyond the outer longitudinal periphery of the lateral parts. In such a case, prior to use and for the purpose of packaging, they are folded back onto themselves or onto an inner side of the lateral parts in a manner known per se. Alternatively, they may also be disposed as closure pads on the entire circumference within the circumferential limit of the rear lateral parts, as is schematically indicated in FIGS. 8 to 9.

The front and rear lateral longitudinal peripheries 19, 20 of the main part 4 in the context of the present invention are understood to be those longitudinal peripheral regions of the main part onto which the lateral parts 16, 17 are joined so as to form the overlapping regions and beyond which the same extend. The longitudinal extent of the front and rear lateral longitudinal peripheries 19, 20 of the main part 4 thus also define the longitudinal extent of the front region and of the rear region 8 of the disposable incontinence diaper 2. In the event of no front lateral parts being provided, the front region is defined as that portion of the diaper shell that, commencing from a front end of the diaper shell, extends across 30% of the length L1.

Both the front lateral parts 16 as well as the rear lateral parts 17, as well as the main part 4, are formed from a non-woven material, in the illustrated case from a PP spun non-woven, Pegatex S, made by Pegas a.s., Primetická 86, 66904 Znojmo, C Z. The area weight of the non-woven material of the front lateral parts and of the main part is 30 g/m². The area weight of the non-woven material of the rear lateral parts 17 in the illustrated case is 27 g/m². The fiber count of the fibers which in each case form the non-woven material is 2 dtex.

FIGS. 3 and 4 show a further disposable incontinence diaper 2a according to the invention. In the following, only those components and construction features which differentiate the disposable incontinence diaper 2a from the one illustrated in FIGS. 1 and 2 will be described. The top sheet 64 of the absorbent insert 5 is configured in a tripartite manner. The top sheet 64 is composed of a first non-woven central strip 14, which is disposed so as to be centric in a central manner above the absorbent body 7, and two non-woven outer strips 15 which are disposed so as to be on either side thereof. The non-woven strips 14, 15 are interconnected in an unreleasable manner by means of a third application of hot-melt adhesive 9 which preferably extends across the entire length of the absorbent insert 5. However, inwardly oriented distal longitudinal peripheral regions 23 of the non-woven outer strips 15 remain unconnected, at least in the crotch region.

These distal longitudinal peripheral regions 23, at least in the crotch region, are connected to at least one pre-tensioned elastic thread 24 which extends in the longitudinal direction. On account thereof, the distal longitudinal peripheral regions 23 can stand upright in a manner known per se from an upper side (inner side which faces the body) of the absorbent insert 5 (in the direction Z) in order to form lateral leakage barriers.

The absorbent insert 5 in the transverse direction is configured so as to be continuously wider than the main part 4 of the diaper shell 3. The absorbent insert 5 in the transverse direction 22 thus completely overlies the first and second overlapping regions 40, 41 and there, in the overlapping regions 40, 41, by way of its outer side, is fixed in a planar manner on the diaper shell 3 (interrupted hatched regions in FIG. 3). Consequently, the absorbent insert 5 along at least an imaginary line which runs in the transverse direction (and which in the illustrated case in an exemplary manner coincides with the section line A-A) overlaps both a respective inner longitudinal periphery 18a of the rear lateral parts 16 as well as a respective rear lateral longitudinal periphery 20 of the main part 4, and there, along this line, is also connected to the inner side of the diaper shell 3. In an analogous manner, the absorbent insert 5 at least along an imaginary line which runs in the transverse direction (not illustrated in FIG. 3) overlaps both a respective inner longitudinal periphery 18b of the front lateral parts 17 as well as a respective front lateral longitudinal periphery 19 of the main part 4, and there, along this line, is also connected to the inner side of the diaper shell 3. The absorbent insert 5 here in the transverse direction 22 outwardly extends by the dimension D beyond the front and rear lateral longitudinal peripheries 19, 20 of the main part 4. D here is 15 mm.

Figure 6:
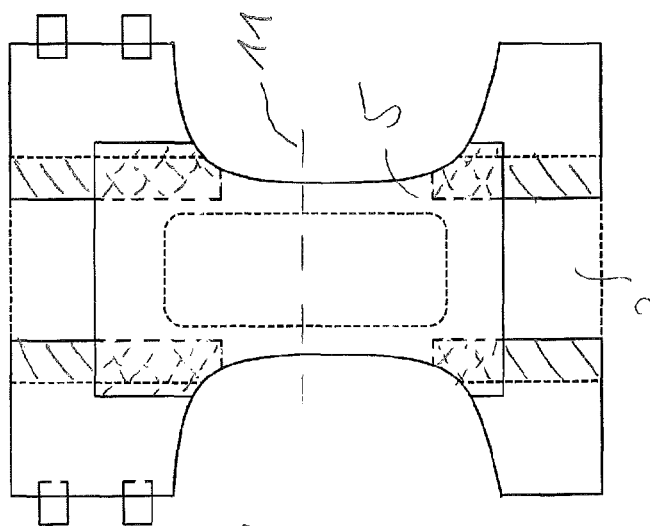
Figure 7:
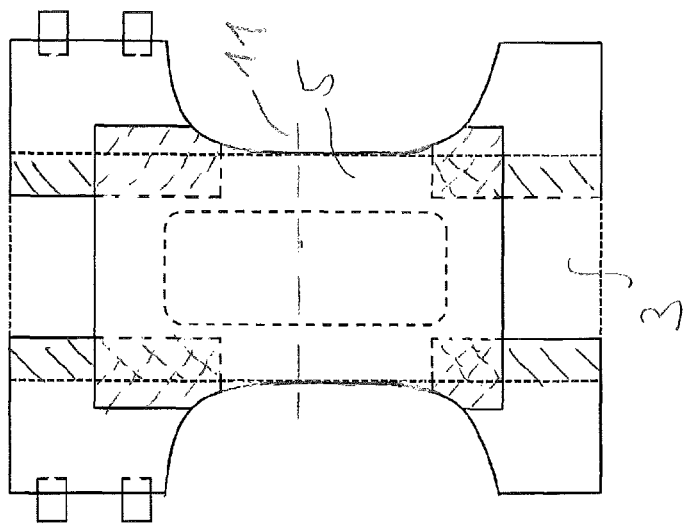

The embodiments of disposable incontinence diapers according to the invention illustrated in FIGS. 1 to 4 in each case have rectangular lateral parts 16, 17, one rectangular main part 4, and one rectangular absorbent insert 5. It is conceivable and advantageous in order to further improve the fit of the diaper to provide the disposable incontinence diaper with a contoured, rounded leg-opening contour. Here, in each case one transverse periphery of the rear and/or front lateral parts 16, 17 which face(s) the crotch region, the lateral longitudinal peripheries of the main part 4, or the absorbent insert 5 may be provided with a contour which at least in portions is rounded. FIGS. 5 to 7 schematically show some of the conceivable embodiments. In this way, the absorbent insert 5 of all embodiments according to FIGS. 5 to 7 is provided in an exemplary manner with a leg-opening contour which at least in portions is rounded in such a manner that the absorbent insert 5 in a region which is close to a transverse center axis 11 of the diaper shell 3 (which axis divides the diaper shell into two halves of equal length) has a smaller transverse extent than in the rear region and the front region. Moreover, FIG. 6 and show a disposable incontinence diaper of which the diaper shell 3 has a leg-opening contour which at least in portions is rounded in such a manner that the diaper shell 3 in a region which is close to the transverse center axis 11 of the diaper shell 3 has a smaller transverse extent than in the back region and the front region. While according to FIG. 7 only the lateral parts have a rounded leg-opening contour, FIG. 6 shows a rounded leg-opening contour which extends continuously through lateral parts, the main part and the absorbent insert 5.

According to a further preferred variant of the invention it is provided for a group of disposable incontinence diapers, which comprises at least first and second such disposable incontinence diapers as described above, to be provided, wherein the first and second disposable incontinence diapers in respect of the dimensions in the longitudinal and transverse directions, in particular also in respect of further properties such as material composition or area weight of the main part and/or the rear lateral parts, have an identical diaper shell, wherein a first absorbent insert of the first disposable incontinence diapers differs from a second absorbent insert of the second disposable incontinence diapers at least in one property selected from the group of dimensions in the longitudinal and/or transverse directions, absorptivity (measured according to ISO 11948-1 (1996)), material composition, layer construction, elastification. It is thus provided that diaper shells of identical construction are used for different absorbent inserts. FIG. 8 schematically visualizes the positioning and fixing of first 5a and second 5b absorbent inserts on a diaper shell 3 which in each case is of identical construction, that is to say identical in respect of all properties. The first absorbent insert 5a differs from the second absorbent insert 5b at least in respect of its dimensions in the longitudinal and transverse directions.

According to a further variant it is provided for a group of disposable incontinence diapers, which comprises first and second disposable incontinence diapers according to the invention, to be provided, wherein the first and second disposable incontinence diapers have an absorbent insert which is identical in respect of at least the dimensions in the longitudinal and transverse directions, wherein the diaper shell of the first disposable incontinence diapers differ from the diaper shell of the second disposable incontinence diapers at least in one property selected from the group of dimensions in the longitudinal and/or transverse directions, material composition, area weight of the main part and/or of the rear lateral parts. FIG. 9 schematically visualizes the positioning and fixing of first absorbent inserts 5 which are of identical construction on first 3a and second 3b diaper shells which differ from one another in respect of their dimensions in the longitudinal and transverse directions.

The invention claimed is:

1. An absorbent disposable incontinence diaper (2, 2a) of the open type, having an at least tripartite diaper shell (3) which has an inner side (30) and an outer side (31), wherein
the diaper shell comprises a main part (4), and at least two separate rear lateral parts (16),
the main part (4) has a front region (6), a rear region (8), and a crotch region (12) which in the longitudinal direction (21) is therebetween to come to lie between the legs of a user,
the rear lateral parts (16) are disposed on both sides of the rear region (8) of the main part (4) in such a manner that the rear lateral parts (16), by way of their outer side, are fixed in first overlapping regions (40) on the inner side of the main part (4) along rear lateral longitudinal peripheries (20), the rear lateral parts (16) in the transverse direction (22) extend beyond the rear lateral longitudinal peripheries (20) of the main part (4), the rear lateral parts (16) have closure means (10), and which closure means (10) extend in the transverse direction (22) beyond an outside edge of the rear lateral parts (16) which outside edge is located in an opposite transverse direction of the location of the rear lateral longitudinal peripheries (20), and wherein the closure means (10) are variable in the positioning in respect of the transverse direction (22) on the outer side (31) of the front region (6) of the diaper, so that a user has the possibility to adapt the diaper to the anatomical profile of the user, the main part (4) and the rear lateral parts (16) comprise a non-woven material or are formed therefrom, the diaper shell (3) continuously extends across a length L1, from a front end (33) of the diaper shell (3) across the crotch region (12) to a rear end (34) of the diaper shell (3), an absorbent insert (5) having an inner side and an outer side is disposed on the inner side (30) of the diaper shell (3), the absorbent insert (5) comprises a fluid-impermeable back sheet (62) and a top sheet (64) between which an absorbent body (7) is disposed, the absorbent insert (5) extends into the first overlapping regions (40) and there, by way of its outer side, is at least in portions fixed on the diaper shell (3), and the absorbent insert (5) has a length L2, and wherein L2<L1 applies, and wherein at least 20%, of the first overlapping regions (40) is connected to the absorbent insert (5).

2. The absorbent disposable incontinence diaper (2, 2a) as claimed in claim 1, having front lateral parts (17) which are separate from one another and disposed on the front region (6) of the main part (4), wherein the front lateral parts (17) are disposed on both side of the front region (6) of the main part (4) in such a manner that the front lateral parts (17), by way of their outer side, are fixed in second overlapping regions (41) on the inner side of the main part (4) along front lateral longitudinal peripheries (19), and the front lateral parts (17) in the transverse direction (22) extend beyond the front lateral longitudinal peripheries (19) of the main part (4).

3. The absorbent disposable incontinence diaper (2, 2a) as claimed in claim 2, wherein the absorbent insert (5) extends into the second overlapping regions (41) and there, by way of its outer side, is at least in portions fixed on the diaper shell (3).

4. The absorbent disposable incontinence diaper (2, 2a) as claimed in claim 3, wherein the back sheet (62) and/or the top sheet (64) in the transverse direction (22) and/or in the longitudinal direction (15) form an overhang (66) over the absorbent body (7), and part-regions of the overhang (66) extend into the first and/or second overlapping regions (40, 41) and there, by way of their outer side, is at least in portions fixed on the diaper shell (3).

5. The absorbent disposable incontinence diaper (2, 2a) as claimed in claim 4, wherein at least 20% of the area of the first overlapping regions (40) is connected to the absorbent insert (5).

6. The absorbent disposable incontinence diaper (2, 2a) as claimed in claim 3, wherein at least 20% of the area of the first overlapping regions (40) is connected to the absorbent insert (5).

7. The absorbent disposable incontinence diaper (2, 2a) as claimed in claim 2, wherein at least 10%, of the area of the second overlapping regions (41) is connected to the absorbent insert (5).

8. The absorbent disposable incontinence diaper (2, 2a) as claimed in claim 2, wherein the proportion of that area of the second overlapping regions (41) that is connected to the absorbent insert (5) is in each case smaller than the proportion of that area of the first overlapping regions (40) that is connected to the absorbent insert (5).

9. The absorbent disposable incontinence diaper (2, 2a) as claimed in claim 2, wherein the back sheet (62) and/or the top sheet (64) in the transverse direction (22) and/or in the longitudinal direction (15) form an overhang (66) over the absorbent body (7), and part-regions of the overhang (66) extend into the first and/or second overlapping regions (40, 41) and there, by way of their outer side, is at least in portions fixed on the diaper shell (3).

10. The absorbent disposable incontinence diaper (2, 2a) as claimed in claim 9, wherein at least 20% of the area of the first overlapping regions (40) is connected to the absorbent insert (5).

11. The absorbent disposable incontinence diaper (2, 2a) as claimed in claim 1, wherein the back sheet (62) and/or the top sheet (64) in the transverse direction (22) and/or in the longitudinal direction (15) form an overhang (66) over the absorbent body (7), and part-regions of the overhang (66) extend into the first and/or second overlapping regions (40, 41) and there, by way of their outer side, is at least in portions fixed on the diaper shell (3).

12. The absorbent disposable incontinence diaper (2, 2a) as claimed in claim 11, wherein at least 20% of the area of the first overlapping regions (40) is connected to the absorbent insert (5).

13. The absorbent disposable incontinence diaper (2, 2a) as claimed in claim 1, wherein the ratio L2/L1 is <0.9.

14. The absorbent disposable incontinence diaper (2, 2a) as claimed in claim 1, wherein the absorbent body (7) does not extend into the first overlapping regions (40).

15. The absorbent disposable incontinence diaper (2, 2a) as claimed in claim 1, wherein the absorbent insert (5) completely overlies the first overlapping regions (40) in the transverse direction (22).

16. The absorbent disposable incontinence diaper (2, 2a) as claimed in claim 1, wherein the absorbent insert 5 has a leg-opening contour which is, at least in portions, rounded or curved, in such a manner that the absorbent insert (5) in a region which is level with a transverse center axis (11) of the diaper shell (3) has a smaller transverse extent than in the rear region (8) and/or the front region (6).

17. The absorbent disposable incontinence diaper (2, 2a) as claimed in claim 1, wherein the diaper shell (3) has a leg-opening contour which is, at least in portions, rounded or curved, in such a manner that the diaper shell (3) in a region which is level with the transverse center axis (11) of the diaper shell (3) has a smaller transverse extent than in the rear region (8) and/or the front region (6).

18. A group of disposable incontinence diapers, which comprises at least first and second such disposable incontinence diapers as claimed in claim 1, wherein the first and second disposable incontinence diapers in respect of the dimensions in the longitudinal and/or transverse directions, have an identical diaper shell (3), and the absorbent insert (5a) of the first disposable incontinence diapers differs from the absorbent insert (5b) of the second disposable incontinence diapers at least in one property selected from the group of dimensions in the longitudinal and/or transverse directions, absorptivity (measured according to ISO 11948-1 (1996)), material composition, layer construction and elastification.

19. The group of disposable incontinence diapers, which comprises at least first and second disposable incontinence diapers as claimed in claim 1, wherein the first and second disposable incontinence diapers have an absorbent insert (5) which is identical in respect of the dimensions in the longitudinal and/or transverse directions, and the diaper shell (3*a*) of the first disposable incontinence diapers differ from the diaper shell (3*b*) of the second disposable incontinence diapers at least in one property selected from the group of dimensions in the longitudinal and/or transverse directions, material composition, area weight of the main part and/or of the rear lateral parts.

20. The absorbent disposable incontinence diaper (2, 2*a*) of claim 1, wherein the closure means (10) are fixable on the entire outer side (31) of the front region (6) of the main part (4).

21. The absorbent disposable incontinence diaper (2, 2*a*) of claim 1, wherein the diaper is in the absence of fix-point fasteners.

\* \* \* \* \*